US007933656B2

(12) United States Patent
Sieracki et al.

(10) Patent No.: US 7,933,656 B2
(45) Date of Patent: Apr. 26, 2011

(54) DISTRIBUTED SYSTEM FOR NEUROSTIMULATION THERAPY PROGRAMMING

(75) Inventors: Jeffrey M. Sieracki, Silver Spring, MD (US); Kim R. Fowler, Windsor Mill, MD (US); Richard B. North, Baltimore, MD (US)

(73) Assignee: Medtronic, Inc., Minneapolis, MN (US)

( * ) Notice: Subject to any disclaimer, the term of this patent is extended or adjusted under 35 U.S.C. 154(b) by 1126 days.

(21) Appl. No.: 11/698,342

(22) Filed: Jan. 26, 2007

(65) Prior Publication Data

US 2007/0123956 A1 May 31, 2007

Related U.S. Application Data

(63) Continuation of application No. 10/696,494, filed on Oct. 29, 2003, now Pat. No. 7,181,286.

(60) Provisional application No. 60/503,222, filed on Sep. 15, 2003, provisional application No. 60/422,263, filed on Oct. 31, 2002, provisional application No. 60/422,264, filed on Oct. 31, 2002.

(51) Int. Cl.
*A61N 1/00* (2006.01)
(52) U.S. Cl. ........................................................ 607/48
(58) Field of Classification Search .................. 607/48, 607/58–60
See application file for complete search history.

(56) References Cited

U.S. PATENT DOCUMENTS

| | | | |
|---|---|---|---|
| 4,926,865 A | 5/1990 | Oman | |
| 5,615,318 A | 3/1997 | Matsuura | |
| 5,938,690 A | 8/1999 | Law et al. | |
| 6,249,705 B1 * | 6/2001 | Snell | 607/59 |
| 6,308,102 B1 | 10/2001 | Sieracki et al. | |
| 6,393,325 B1 | 5/2002 | Mann et al. | |
| 6,480,743 B1 | 11/2002 | Kirkpatrick et al. | |
| 6,597,954 B1 | 7/2003 | Pless et al. | |
| 6,609,032 B1 | 8/2003 | Woods et al. | |
| 6,654,027 B1 | 11/2003 | Hernandez | |
| 6,659,968 B1 | 12/2003 | McClure | |
| 6,662,051 B1 | 12/2003 | Eraker et al. | |
| 6,665,565 B1 | 12/2003 | Stomberg et al. | |

(Continued)

FOREIGN PATENT DOCUMENTS

WO WO 01/03575 1/2001

(Continued)

OTHER PUBLICATIONS

Fowler, K.R., "Neurological Stimulation System", Proceedings AAMI 21st Annual Meeting, Apr. 12-16, p. 27, 1986.

(Continued)

*Primary Examiner* — George Manuel
(74) *Attorney, Agent, or Firm* — Shumaker & Sieffert, P.A.

(57) ABSTRACT

A distributed system comprises a programming device and a remotely located server. During a programming session, the programming device transmits programs and rating information associated with the programs to the server. The server presents the rating information to a clinician to assist the clinician in selecting from among programs tested during the programming session. The programming device may also transmit patient information and device configuration information to the server for storage with selected programs and rating information within a database as part of a patient record. Programs and information received from a plurality of programming devices and for a plurality of patients may be stored in the database and analyzed by the server to provide responses to user queries made by clinicians via programming devices.

21 Claims, 9 Drawing Sheets

U.S. PATENT DOCUMENTS

| | | | |
|---|---|---|---|
| 7,015,935 | B2 | 3/2006 | Herget et al. |
| 7,142,923 | B2 | 11/2006 | North et al. |
| 7,146,219 | B2 | 12/2006 | Sieracki et al. |
| 2001/0007950 | A1 | 7/2001 | North et al. |
| 2002/0116036 | A1 | 8/2002 | Daignault, Jr. et al. |
| 2004/0136578 | A1 | 7/2004 | Sieracki et al. |
| 2004/0138724 | A1 | 7/2004 | Sieracki et al. |
| 2005/0119714 | A1 | 6/2005 | Sieracki et al. |

FOREIGN PATENT DOCUMENTS

| | | |
|---|---|---|
| WO | WO 01/39831 | 6/2001 |
| WO | WO 01/43823 | 6/2001 |
| WO | WO 01/47600 | 7/2001 |

OTHER PUBLICATIONS

Fowler, K. R., North, R.B.: "Patient-interactive PC interface to implanted, multichannel stimulators," Proceedings of 39th Annual Conference on Engineering in Medicine and Biology, p. 380, 1986.

North, R.B., Fowler, K.R., "Computer-controlled, patient-interactive, multichannel, implanted neurological stimulators," Applied Neurophysiology, 50:39-41, 1987.

North, R.B., Nigrin, D.J., Szymanski, R.E., Fowler, K.R., "Computer-controlled, multichannel, implanted neurological stimulation system: Clinical assessment," Pain (Suppl.), 5:S83, 1990.

Fowler, K.R., North, R.B., "Computer-optimized neurological stimulation," Proc. Ann. Internat. Conf. IEEE Engineering Medicine and Biology Soc., 13:1692-1693, 1991.

Fowler, K.R., North, R.B., "Computer-optimized neurostimulation," APL Technical Digest, 12:192-197, 1991.

North, R.B., et al., "Spinal cord stimulation for chronic intractable pain: superiority of 'multi-channel' devices," Pain, V44, pp. 119-130, 1991.

North, R.B., Fowler, K.R., "Computer-controlled, patient-interactive neurological stimulation system," (Abstract) Acta Neurochir, 117:90, 1992.

North, R.B., Fowler, K.R., Nigrin, D.A., Szymanski, R.E., "Patient interactive, computer-controlled neurological stimulation system: Clinical efficacy in spinal cord stimulator adjustment," Journal of Neurosurgery, 76:967-972, 1992.

North, R.B.., Fowler, K.R., Nigrin, D.A., Szymanski, R.E., Piantadosi, S., "Automated 'pain drawing' analysis by computer-controlled, patient-interactive neurological stimulation system," Pain, 50:51-57, 1992.

North, R.B., "Spinal Cord Stimulation for Chronic Intractable Pain," Electrical and Magnetic Stimulation of the Brain and Spinal Cord, pp. 289-301, 1993.

North, R.B., "The Role of Spinal Cord Stimulation in Contemporary Pain Management," APS Journal, vol. 2, No. 2, pp. 91-99, 1993.

North, R. B., Kidd, D. H., Zahurak, M., James, C. S., Long, D. M., "Spinal cord stimulation for chronic, intractable pain: Experience over two decades," Neurosurgery, 32:384-395, 1993.

North, R.B., Fowler, K.R., "Patient-interactive, microprocessor-controlled neurological stimulation system" (abstract), Stereotactic and Functional Neurosurgery, 62:309-315, 1994.

North, R. B., Levy, R. M., Consensus conference on the neurosurgical management of pain; Neurosurgery, 34:756-761, 1994.

North, R. B., Kidd, D. H., Lee, M. S., Piantadosi, S., "A prospective, randomized study of spinal cord stimulation versus reoperation for the failed back surgery syndrom," Stereotactic and Functional Neurosurgery, 62:267-272, 1994.

North, R.B., et al., "Spinal Cord Stimulation for Chronic Pain," Functional Neurosurgery, vol. 6, No. 1, pp. 145-155, Jan. 1995.

North, R.B., Cutchis, P., "Spinal cord stimulation for chronic intractable pain," Spinal Cord Stimulation II, pp. 49-63, Darmstadt, Steinkopff, 1995.

North, R.B., McNamee, P., Wu, L., Piantadosi,S., "Artificial neural networks: Application to electrical stimulation of the human nervous system," (abstract) Stereotactic and Functional Neurosurgery, 65:161, 1995.

North, R. B., Kidd, D. H., Wimberly, R. L., Edwin, D., "Prognostic value of psychological testing in spinal cord stimulation patients: A prospective study," Neurosurgery, 39:301-311, 1996.

North, R. B., Kidd, D. H., Zahurak, M., Piantadosi, S., "Specificity of diagnostic nerve blocks: A prospective, randomized study of sciatica due to lumbosacral spine disease," Pain, 65:77-85, 1996.

North, R.B., McNamee, P., Wu,L., Piantadosi, S., "Artificial neural networks: Application to electrical stimulation of the human nervous system," Neurosurgical Focus, 2(1:1):1-5, 1997.

Alo, K. M. et al., "Computer Assisted and Patient Interactive Programming of Dual Octrode Spinal Cord Stimulation in the Treatment of Chronic Pain," Neuromodulation, vol. 1, No. 1, pp. 30-45, 1998.

North, R.B., Sieracki, J.N., Fowler, K.R., Alvarez, B., Cutchis, P.N., "Patient-interactive, microprocessor-controlled neurological stimulation system," Neuromodulation, 1(4):185-193, 1998.

Khalessi, A. A., Taylor, R. S., Brigham, D. D., North, R. B., "Automated, patient-interactive spinal cord stimulator adjustment: A cost-minimization analysis," Neurosurgery, 53:501-502, 2003.

North, R. B., Calkins, S. K., Campbell, D. S., Sieracki, J. M., Piantadosi, S. A., Daly, M. J., Dey, P. B., Barolat, G., "Automated, patient-interactive spinal cord stimulator adjustment: A randomized, controlled trial," Neurosurgery 52:572-580, 2003.

* cited by examiner

DISTRIBUTED SYSTEM FOR NEUROSTIMULATION THERAPY PROGRAMMING

This application is a continuation of U.S. application Ser. No. 10/696,494, filed Oct. 29, 2003, which claims the benefit of U.S. Provisional Application Ser. No. 60/422,263, filed Oct. 31, 2002, U.S. Provisional Application Ser. No. 60/422,264, filed Oct. 31, 2002, and U.S. Provisional Application Ser. No. 60/503,222, filed Sep. 15, 2003. The entire content of these Applications is incorporated herein by reference.

TECHNICAL FIELD

The invention relates to neurostimulation therapy, and more particularly, to programming of implantable medical devices that deliver neurostimulation therapy.

BACKGROUND

Implantable medical devices are used to deliver neurostimulation therapy to patients to treat a variety of symptoms or conditions such as chronic pain, tremor, Parkinson's disease, epilepsy, incontinence, or gastroparesis. Typically, implantable medical devices deliver neurostimulation therapy in the form of electrical pulses via leads that include electrodes. To treat the above-identified symptoms or conditions, for example, the electrodes may be located proximate to the spinal cord, pelvic nerves, or stomach, or within the brain of a patient.

Typically, a clinician uses a programmer, e.g., a computing device capable of communicating with implantable medical devices via device telemetry, to program an implantable medical device for delivery of neurostimulation therapy to a patient. In some cases, such clinician programmers take the form of handheld and/or tablet-type computing devices. Handheld and/or tablet-type clinician programmers can allow for a more natural "bedside" interaction between clinicians and patients during the programming process. Handheld and/or tablet-type clinician programmers can also allow the programmer to be handed off to the patient for entry of symptom and/or efficacy data, e.g., for patient-interactive programming as described in U.S. Pat. No. 6,308,102, issued to Sieracki et al. (hereinafter the Sieracki '102 patent), which is incorporated herein by reference in its entirety.

During the programming process, a clinician may select values for a number of programmable parameters in order to define the neurostimulation therapy to be delivered to a patient. For example, the clinician may select a voltage or current amplitude and pulse width for a stimulation waveform to be delivered to the patient, as well as a rate at which the pulses are to be delivered to the patient. The clinician may also select as parameters particular electrodes within an electrode set to be used to deliver the pulses, and the polarities of the selected electrodes. A group of parameter values may be referred to as a program in the sense that they drive the neurostimulation therapy to be delivered to the patient. The process of selecting values for the parameters that provide adequate results can be time consuming, and may require a great deal of trial and error before one or more "best" programs, e.g., programs that are better in terms of clinical efficacy versus side effects experienced than other programs tested, are discovered. The clinician may be required to make notations describing a number of programs and feedback received from the patient regarding the perceived efficacy of each program. In some cases, the clinician collects detailed graphical information describing patient symptoms and program efficacy, e.g., pain and paresthesia maps as described in the Sieracki '102 patent. In some cases, such as the patient-interactive programming systems described in the Sieracki '102 patent, complicated algorithms provide automated or semi-automated routines that involve generation of numerous potential programs with complex stimulus patterns, testing of the programs, and recordation of efficacy information for the programs.

SUMMARY

In general, the invention is directed to techniques for management of information during programming of neurostimulation therapy. A distributed system for neurostimulation therapy programming includes a local programming device, such as a clinician programmer, and a network device, such as a server that maintains a database. In some cases, and particularly in cases where the clinician programmer takes the form of a handheld and/or tablet based computing device, the burden of executing complex programming algorithms, and/or the burden storing the wealth of information generated during the programming process for a number of patients, may be too great for the local programming device to bear alone. Consequently, according to the invention, the programming device interacts with the network device such that the network device bears at least a portion of these burdens.

During a programming session, the programming device transmits programs and rating information associated with the programs to the server. The programming device may transmit program parameters for programs specified by the clinician to the server. The server may direct the programming device to control delivery of neurostimulation by an implantable neurostimulator implanted within a patient according to the specified programs. In some embodiments, the server randomizes or otherwise selects an order for testing of specified programs, and directs the programming device to test the programs in the specified order.

The programming device may collect rating information for a tested program during and/or immediately after delivery of that program, and may transmit the rating information to the server after collection. In exemplary embodiments, the programming device displays body templates that depict a surface of the human body, and receives input from one or both of the clinician and patient that indicates regions on the templates associated with an area of pain and with areas of paresthesia provided by each program. Information describing the regions is transmitted to the server, and the server calculates an amount of overlap of paresthesia and pain provided by each program as rating information for the programs.

The server presents the rating information to a clinician to assist the clinician in selecting from among programs tested during the programming session. The programs and rating information may be presented to the clinician as a list of tested programs generated by the server and displayed by the programming device. The server may receive selections made from the list by the clinician of one or more programs for long-term use by the implantable neurostimulator in delivering therapy to the patient.

The server stores selected programs and associated rating information within a database as part of a patient record. The programming device may also transmit patient information and device configuration information to the server for storage with selected programs and rating information within a database as part of the patient record. Programs and information received from a plurality of programming devices and for a plurality of patients may be stored in the database and analyzed by the server to provide responses to user queries made by clinicians via programming devices. For example, the server may compare patient and device configuration information for a current patient received as part of a query to patient and device configuration information stored records within the database, and suggest one or more programs for the current patient based on the comparison. In some embodiments, clinicians, patients, researchers, or other interested parties can access one or more patient records or submit queries to the server via other computing devices, such as desktop computers, laptop computers, or personal digital assistants (PDAs).

In one embodiment, the invention is directed to a system comprising a programming device to control delivery of neurostimulation by an implantable neurostimulator implanted within a patient during a programming session, and a server connected to the programming device via a network during the programming session. The server directs the programming device to control the implantable neurostimulator to deliver neurostimulation according to a plurality of programs during the programming session, receives rating information for each of the programs via the programming device, the rating information for each of the delivered programs relating to the efficacy of that program, and presents the rating information to a clinician via the programming device to assist the clinician in selection of one or more of the programs for long-term programming of the implantable neurostimulator.

In another embodiment, the invention is directed to a method in which a programming device is directed via a network to control an implantable neurostimulator to deliver neurostimulation according to a plurality of programs during a programming session, the implantable neurostimulator implanted within a patient. The method further comprises receiving rating information for each of the programs via the programming device and the network, the rating information for each of the delivered programs relating to the efficacy of that program, and presenting the rating information to a clinician via the network and the programming device to assist the clinician in selection of one or more of the programs for long-term programming of the implantable neurostimulator.

In a further embodiment, the invention is directed to a computer-readable medium containing instructions. The instructions cause a programmable processor to direct a programming device via a network to control an implantable neurostimulator to deliver neurostimulation according to a plurality of programs during a programming session, the implantable neurostimulator implanted within a patient. The instructions further cause a programmable processor to receive rating information for each of the programs via the programming device and the network, the rating information for each of the delivered programs relating to the efficacy of that program, and present the rating information to a clinician via the network and the programming device to assist the clinician in selection of one or more of the programs for long-term programming of the implantable neurostimulator.

The invention may provide advantages. For example, by placing a portion of the storage and computation burdens associated with programming of implantable neurostimulators on a networked component, the distributed system may allow for greater complexity of programming algorithms and or reduction in the size and complexity of clinician programmers. For example, computationally complex analysis of pain and paresthesia maps can be performed by the server to provide rating information to the clinician. The storage burden on the clinician programming device is reduced by storing the data of a patient record, particularly of the rather large pain and paresthesia maps, on a remote database.

Further, the server allows a plurality of clinicians to treat a plurality of patients in various locations around the world at various times. Storage of programs within a common database allows for sharing stimulation treatment information, which can allow a clinician to provide better results for any particular patient. Storage of programs, rating information, patient information, and device configuration information for a plurality of patients also allow for analysis of the collected information and provision of useful information to the clinician, such as suggested programs or programming protocols that have been effective is situations similar to that currently faced by the clinician. Using the information stored in the database, the server may provide information that results in testing fewer programs, consequently reducing the time required of the clinician and patient to program a neurostimulation device controlling the delivery of neurostimulation therapy to the patient. Additionally, information collected from a large number and variety of cases could be a useful resource for academic and/or commercial research.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
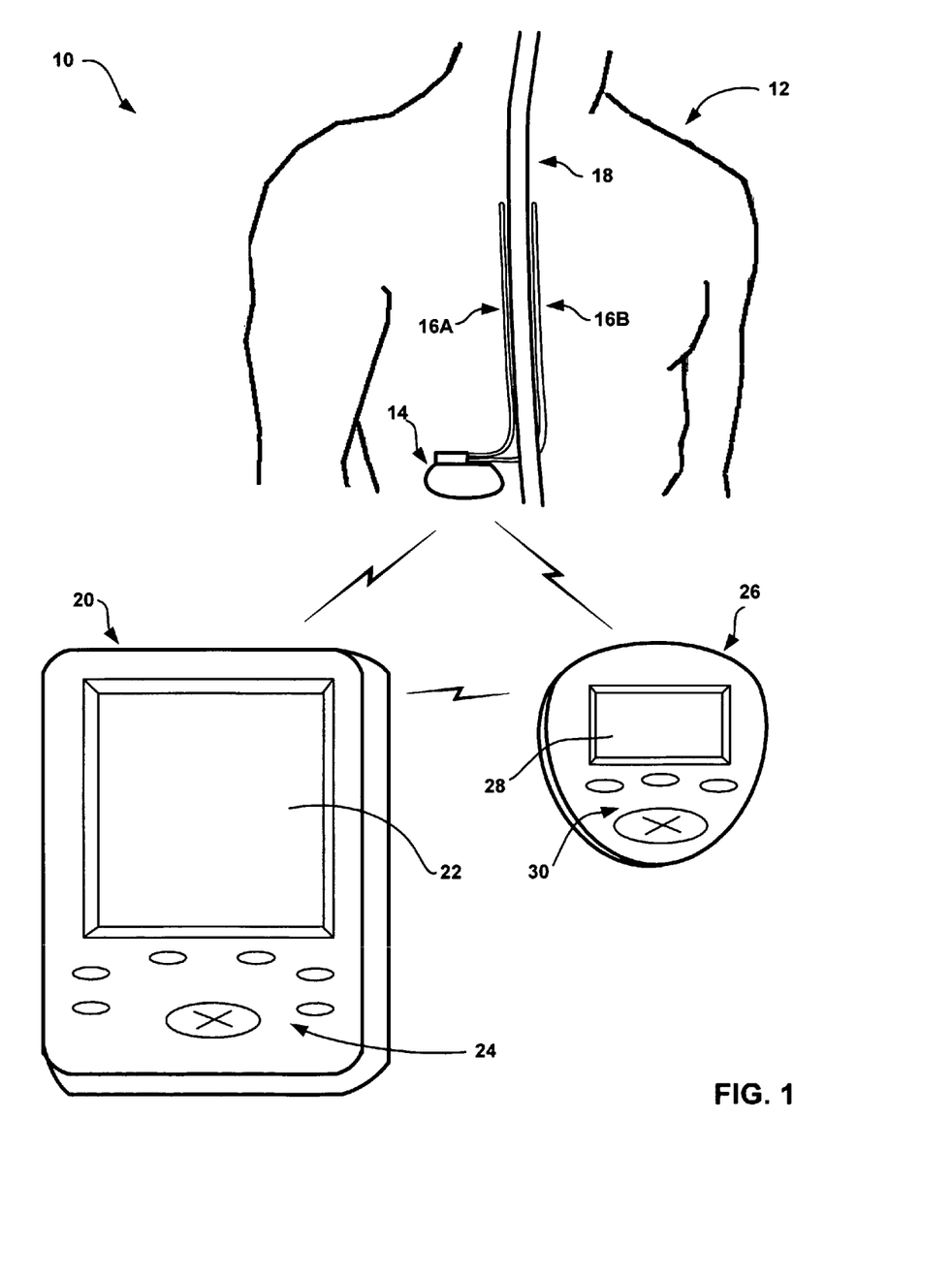
FIG. 1 is a conceptual diagram illustrating an example environment in which an implantable neurostimulator implanted within a patient is programmed to provide neurostimulation therapy to the patient.

FIG. 1 is a diagram illustrating an example environment 10 in which an implantable neurostimulator (INS) 14 implanted within a patient 12 is programmed to provide neurostimulation therapy to patient 12. INS 14 may be an implantable pulse generator, and may deliver neurostimulation therapy to patient 12 in the form of electrical pulses.

INS 14 delivers neurostimulation therapy to patient 12 via leads 16A and 16B (collectively "leads 16"). Leads 16 may, as shown in FIG. 1, be implanted proximate to the spinal cord 18 of patient 12, and INS 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from INS 14 to the brain (not shown) of patient 12, and INS 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and INS 14 may deliver neurostimulation therapy to treat incontinence or gastroparesis.

INS 14 delivers neurostimulation therapy according to a selected program. Each program may include values for a number of parameters, the parameter values defining the neurostimulation therapy delivered according to the selected program. In embodiments where INS 14 delivers neurostimulation therapy in the form of electrical pulses, the parameters may include voltage or current pulse amplitudes, pulse widths, pulse rates, and the like. Further, each of leads 16 includes electrodes (not shown in FIG. 1), and the parameters for a program may include information identifying which electrodes have been selected for delivery of pulses according to the program, and the polarities of the selected electrodes.

System 10 also includes a clinician programmer 20. Clinician programmer 20 may, as shown in FIG. 1, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22 using a stylus (not shown). A user may also interact with clinician programmer 20 using peripheral pointing devices, such as a mouse. Keypad 24 may take the form of an alphanumeric keypad or a reduced set of keys associated with particular functions.

A clinician (not shown) may use clinician programmer 20 to program neurostimulation therapy for patient 12. In general, a clinician programs neurostimulation therapy for patient 12 by specifying one or more programs, e.g., by selecting parameter values for one or more programs, to be used by INS 14 for delivery of neurostimulation to patient 12. During a programming session, a number of programs are tested on patient 12, e.g., clinician programmer 20 directs INS 14 to deliver neurostimulation therapy to patient 12 according to each program. The clinician selects one or more of the tested programs for use by INS 14 in delivering neurostimulation therapy to patient 12.

As will be described in greater detail below, clinician programmer 20 communicates with a server and a database via a network connection during a programming session. Clinician programmer 20 may transmit information collected during the programming session to the server for storage on the database. Further, clinician programmer 20 may send programs specified by the clinician for testing during the programming session to the server, may be controlled during the programming session by the server, and may send the server information identifying which programs the clinician has selected from among those tested during the programming session. Clinician programmer 20 may also send rating information to the server, such as pain and paresthesia maps for storage and calculation of amounts of overlap provided by the tested programs by the server, as will be described in greater detail below. Clinician programmer 20 may transmit programs and information to the server via the network in real-time during the programming session.

In some embodiments, as will be described in greater detail below, the database may store information for a variety of patients and from a variety of programming sessions, and the clinician may query the server via clinician programmer 20. The query may include information describing characteristics of patient 12 or the configuration of INS 14 and leads 16. In such embodiments, the server compares the information provided with the query to information stored in the database to provide a result, such as a suggested program or procedure, in response to the query. The suggested program or procedure may then, for example, be tested or applied during the programming session for patient 12.

System 10 also includes a patient programmer 26, which also may, as shown in FIG. 1, be a handheld computing device. Patient programmer 26 may also include a display 28 and a keypad 30, to allow patient 12 to interact with patient programmer 26. In some embodiments, display 26 may be a touch screen display, and patient 12 may interact with patient programmer 26 via display 28. Patient 12 may also interact with patient programmer 26 using peripheral pointing devices, such as a stylus or mouse.

Patient 12 may use patient programmer 26 to control the delivery of neurostimulation therapy by INS 14. Patient 12 may use patient programmer 26 to activate or deactivate neurostimulation therapy and, as will be described in greater detail below, may use patient programmer 26 to select which from among a plurality of available programs will be used by INS 14 to deliver neurostimulation therapy. Further, as will be described in greater detail below, patient programmer 26 may interact with the server via the network to update the patient record during times between clinic visits.

INS 14, clinician programmer 20, and patient programmer 26 may, as shown in FIG. 1, communicate via wireless communication. Clinician programmer 20 and patient programmer 26 may, for example, communicate via wireless communication with INS 14 using RF telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary wireless communication protocols. Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of INS 14 and patient programmer 26 via remote telemetry techniques known in the art, communicating via a local area network (LAN), wide area network (WAN), public switched telephone network (PSTN), or cellular telephone network, for example.

Figure 2:
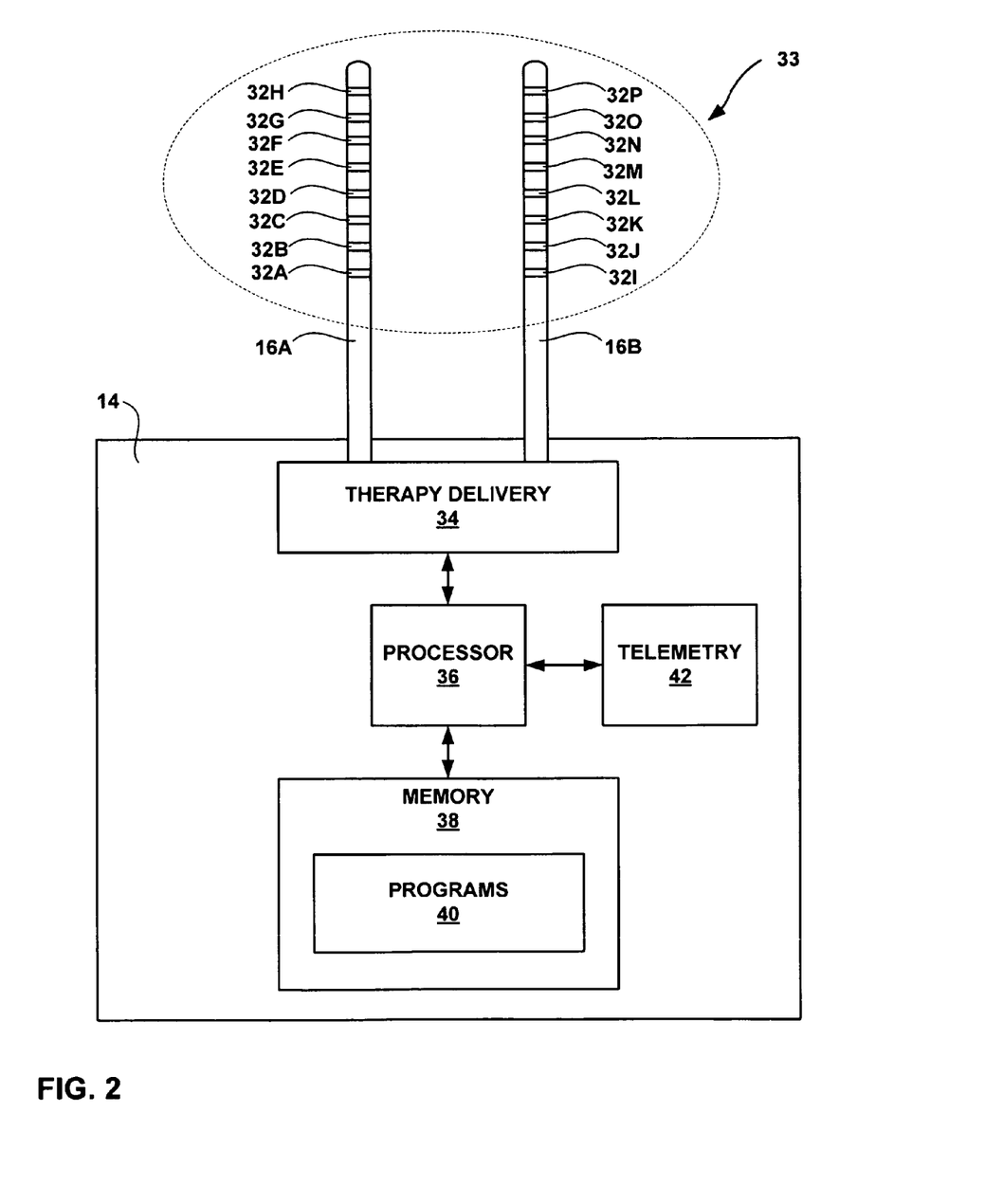
FIG. 2 is a block diagram further illustrating the implantable neurostimulator of FIG. 1.

FIG. 2 is a block diagram illustrating an example configuration of INS 14. INS 14 may deliver neurostimulation therapy via electrodes 32A-H of lead 16A and electrodes 32I-P of lead 16B (collectively "electrodes 32"). Electrodes 32 collectively form a set 33 of electrodes implanted within patient 12 (FIG. 1). Electrodes 32 may be ring electrodes. The configuration, type and number of electrodes 32 within set 33 illustrated in FIG. 2 are merely exemplary.

Electrodes 32 are electrically coupled to a therapy delivery circuit 34 via leads 16. Therapy delivery circuit 34 may, for example, include one or more output pulse generators, e.g., capacitive elements and switches, coupled to a power source such as a battery. Therapy delivery circuit 34 delivers electrical pulses to patient 12 via combination of electrodes 32 from within set 30 that includes two or more active electrodes under the control of a processor 36.

Processor 36 controls therapy delivery circuit 34 to deliver neurostimulation therapy according to a selected program. Specifically, processor 36 may control circuit 34 to deliver electrical pulses with the amplitudes and widths, and at the rates specified by the program. Processor 36 may also control circuit 34 to deliver the pulses via a selected combination of electrodes 32 of set 33, as specified by the program. Processor 36 may include a microprocessor, a controller, a digital signal processor (DSP), an application specific integrated circuit (ASIC), an field programmable gate array (FPGA), discrete logic circuitry, or the like.

INS 14 also includes a memory 38. In the illustrated embodiment, memory 38 stores one or more programs 40 that are available to be selected by processor 36 for delivery of neurostimulation therapy. Memory 38 may also include program instructions that, when executed by processor 36, cause INS 14 to perform the functions ascribed to INS 14 herein. Memory 38 may include any volatile, non-volatile, magnetic, optical, or electrical media, such as a random access memory (RAM), read-only memory (ROM), non-volatile RAM (NVRAM), electrically erasable programmable ROM (EEPROM), flash memory, and the like.

INS 14 also includes a telemetry circuit 42 that allows processor 36 to communicate with clinician programmer 20 and patient programmer 26. Processor 36 receives programs to test on patient 12 from clinician programmer 20 via telemetry circuit 42 during programming by a clinician during a programming session. Processor 36 further receives programs 40 selected by the clinician from among the tested programs from clinician programmer 20 via telemetry circuit 42, and stores the received programs 40, which may be selected by patient 12 via patient programmer 26, within memory 38. In other embodiments, as will be described in greater detail below, a plurality of programs for selection by patient 12 are stored in patient programmer 26, and processor 36 receives the selected program via telemetry circuit 42, stores the selected program in memory 38, which may comprise one or more registers, and uses the selected program to control delivery of neurostimulation therapy by therapy delivery circuit 34.

Figure 3:
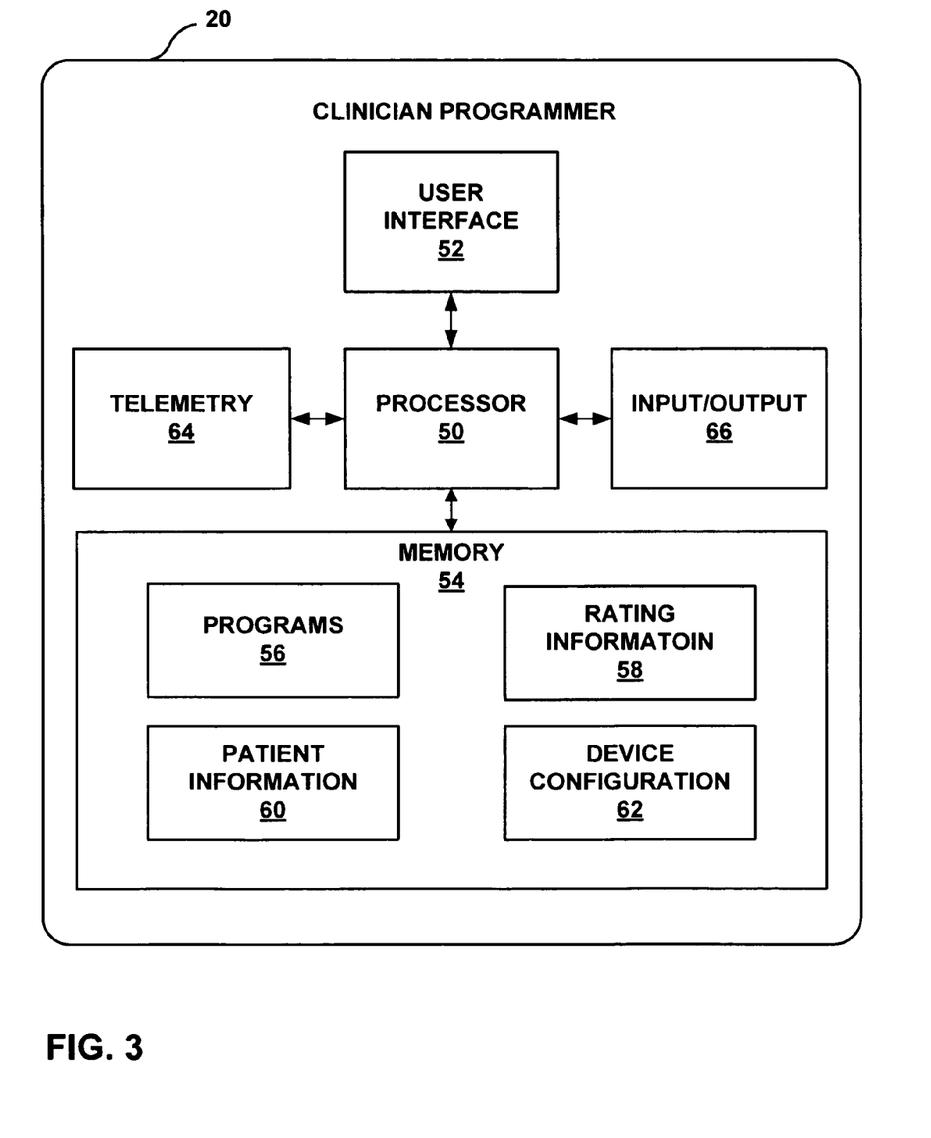
FIG. 3 is a block diagram illustrating an example clinician programmer that allows a clinician to control delivery of neurostimulation therapy to a patient by an implantable neurostimulator during a programming session and to interact with a server.

FIG. 3 is a block diagram illustrating an example configuration of clinician programmer 20. A clinician may interact with a processor 50 via a user interface 52 to program neurostimulation therapy for patient 12 as described herein. User interface 52 may include display 22 and keypad 24, and may also include a touch screen or peripheral pointing devices as described above. Processor 50 may also provide a graphical user interface (GUI) via display 22 to facilitate interaction with a clinician. Processor 50 may include a microprocessor, a controller, a DSP, an ASIC, an FPGA, discrete logic circuitry, or the like.

Clinician programmer 20 also includes a memory 54. Memory 54 may include program instructions that, when executed by processor 50, cause clinician programmer 20 to perform the functions ascribed to clinician programmer 20 herein. Memory 54 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

A clinician may program neurostimulation therapy for patient 12 by specifying programs for testing on patient 12 during a neurostimulation therapy programming session. In some embodiments, the clinician may specify one or more programs for testing by selecting programs suggested as a result of a query to a server, as will be described in greater detail below. The clinician may interact with the GUI and user interface 52 in order to specify programs, and to interact with a server via a network, as will be described in greater detail below.

Processor 50 may store the specified programs 56 within memory 54, and transmits specified programs 56 to the server via I/O circuitry 66. The server directs processor 50 to test specified programs 56 by, for example, providing processor 50 with an order for testing of specified programs 56. To test a specified program 56, processor 50 delivers the program to INS 14 via a telemetry circuit 64 for delivery of neurostimulation according to that program to patient 12.

Upon delivery of a selected or specified program, a processor 50 may receive feedback relating to the tested program via the GUI and user interface 52 from at least one of the clinician and patient 12. For example, processor 50 may receive a numerical score for each program that reflects the effectiveness of that program. In some embodiments, processor 50 may additionally or alternatively receive a pain map, and may receive paresthesia maps for each program. Processor 50 stores numerical scores, a pain map, and/or paresthesia maps as rating information 58, and transmits rating information 58 to the server via I/O circuit 66 and a network.

In order to receive pain and paresthesia maps, processor 50 may retrieve body templates from memory 54 for presentation via display 22. The body templates are images that illustrate a surface of the human body. One or both of the clinician and patient 12 indicate areas of pain and paresthesia experienced by patient 12 by highlighting, shading, or outlining regions of the body templates presented by processor 50. In exemplary embodiments, display 22 is a touch-screen display, and the user indicates one or more regions on each of the body templates using a stylus. Processor 50 stores and transmits information describing the indicated pixel regions of the body templates as a pain map and paresthesia maps. Further information describing techniques for collecting pain and paresthesia maps may be found in the Sieracki '102 patent.

Processor 50 may receive a listing of tested programs 56 and associated rating information 58 from the server for presentation to the clinician via display 22 to facilitate selection of programs. The clinician selects one or more programs for long-term use by INS 14 from the list via user interface 52. Processor 50 provides the selected programs to INS 14 via telemetry circuit 64, and/or to patient programmer 26 via I/O circuit 66. Processor 50 also indicates to the server which of programs 56 were selected by the clinician for long-term use, so that the server can store the selected programs within a database as part of a record for patient 12. The clinician may also select additional effective programs 56 for storage in the patient record within the database, so that they may be selected for programming of INS 14 at a later date.

The clinician may interact with user the GUI and user interface 52 to collect a variety of additional types of information during a programming session. For example, the clinician may enter patient information 60, including age, height, weight, sex, and symptoms. As another example, the clinician may enter device configuration information 62, including a device type of INS 14, a number and type of leads 16, a number of electrodes, the configuration of the electrodes, e.g., their position within the body. Patient information 60 and device configuration information 62 may be stored within memory 54, and are transmitted via I/O circuitry 66 to the server for storage within the database as part of the patient record.

The database stores programs, rating information, patient information, and device configuration information within a plurality of records for a plurality of patients. In some embodiments, the clinician may direct clinician programmer 20 to transmit a query containing specified information to the server via the network connection. In response to the query, the server analyzes the information provided by the query through a comparison to the information stored within the database. The result based on the comparison is received by clinician programmer 20 and may include one or more suggested program, and in some cases, statistics relating to the suggested programs. In exemplary embodiments, the server suggests programs based on a comparison of patient information 60 and/or device configuration information 62 provided as part of the query to the information stored in the database.

In exemplary embodiments, programs 56, rating information 58, patient information 60, and device configuration information 62 are stored in memory 54 only during the programming session, with permanent storage of such information within a database as described above. Because such information is not permanently stored for a plurality of patients within memory 54, memory 54 and clinician programmer 20 may be smaller and less expensive devices. In some embodiments, the information need not be stored in memory 54 at all. Rather, clinician programmer 20 may simply forward the information to the server for storage in the database, and may individually receive programs to test on patient 12 during the programming session from the server as they are to be tested. In various embodiments, I/O circuitry 66 includes transceivers for wireless communication, appropriate ports for wired communication or communication via removable electrical media, appropriate drives for communication via removable magnetic or optical media, a modem, and/or a network interface card.

Figure 4:
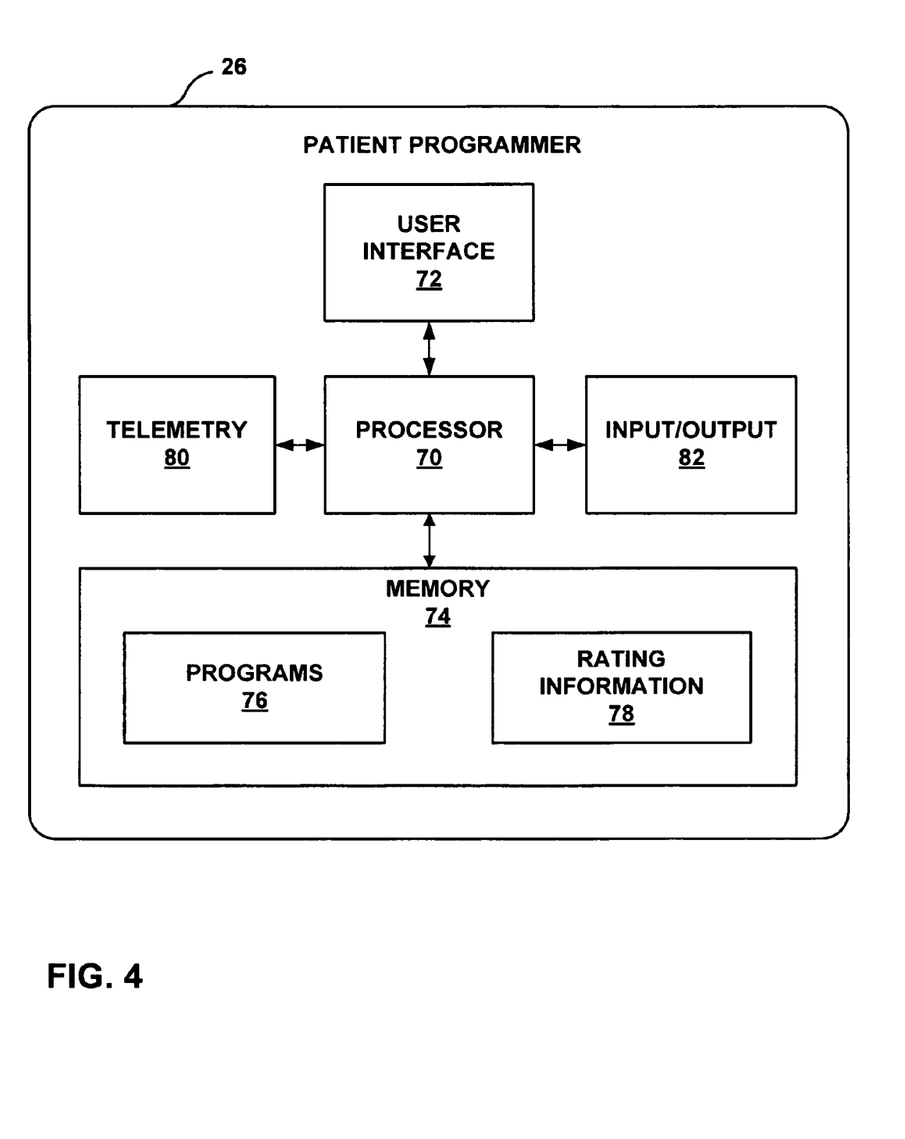
FIG. 4 is a block diagram illustrating an example patient programmer that allows a patient to control delivery of neurostimulation therapy and interacts with the server.

FIG. 4 is a block diagram illustrating an example configuration of patient programmer 26. Patient 12 may interact with a processor 70 via a user interface 72 in order to control delivery of neurostimulation therapy by, for example, starting and stopping delivery of therapy, adjusting parameters of programs, and selecting from among a plurality of available programs. User interface 72 may include display 28 and keypad 30, and may also include a touch screen or peripheral pointing devices as described above. Processor 70 may also provide a graphical user interface (GUI) via display 28 to facilitate interaction with patient 12. Processor 70 may include a microprocessor, a controller, a DSP, an ASIC, an FPGA, discrete logic circuitry, or the like.

Patient programmer 26 also includes a memory 74. In some embodiments, memory 74 may store a plurality of programs 76 that are available to be selected by patient 12 for delivery of neurostimulation therapy. A program selected by patient 12 is delivered to INS 14 via telemetry circuit 80, and used by INS 14 to control delivery of neurostimulation by INS 14.

Between clinic visits, patient 12 may record additional rating information 78 regarding programs 76 during use via user interface 72. Processor 70 may store rating information 78 within memory 74, and may provide the rating information to the server via I/O circuitry 82. Patient 12 may also update other information stored within the database as part of the patient record for patient 12, such as patient information 60, via patient programmer 20.

Memory 74 may also include program instructions that, when executed by processor 70, cause patient programmer 26 to perform the functions ascribed to patient programmer 26 herein. Memory 74 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like. In various embodiments, I/O circuitry 82 may include transceivers for wireless communication, appropriate ports for wired communication or communication via removable electrical media, appropriate drives for communication via removable magnetic or optical media, a modem, and/or a network interface card.

Figure 5:
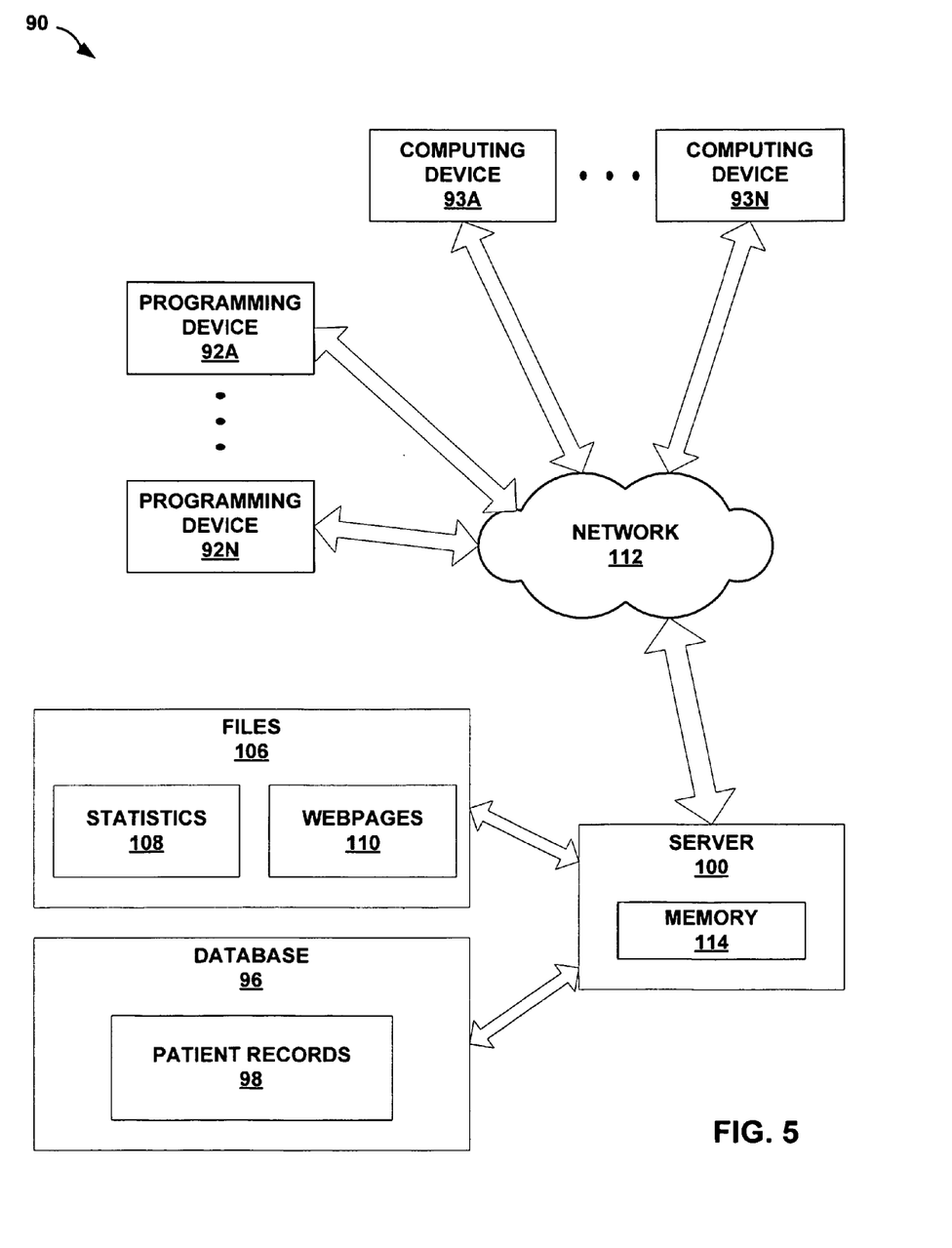
FIG. 5 is a block diagram illustrating an example distributed system comprising a plurality of programming devices and computing devices connected to the server and database via a network.

FIG. 5 is a block diagram illustrating an example distributed system 90 comprising a plurality of programming devices 92A-N (hereinafter programming devices 92) connected to server 100 via a network 112. Programming devices 92 may be clinician programmers 20 or patient programmers 26. Network 112 includes at least one of a local area network (LAN), a wide area network (WAN), the Internet, a wireless network, a cellular telephone network, and a landline telephone network.

Server 100 interacts with programming devices 92 via network 112 as described herein. Server accesses a database 96 that stores programs and information as patient records 98 for a plurality of patients. Patient records 98 may include selected programs 56, associated rating information 58, patient information 60, and device configuration information 62, as described above.

As described above, server 100 may receive queries including information, such as patient information and device configuration information, from programming devices 92, and analyze the information by comparison to information within database 96. A result such as a suggested program or procedure is transmitted to the requesting programming device 92. In some embodiments, server 100, or a human administrator, analyzes patient records 98 in the absence of a specific query and creates files 106 that server 100 may serve to programming devices 92 in response to queries. For example, statistics 108 relating to use or effectiveness or particular programs, procedures, classes or programs, and classes or procedures may be compiled and presented to clinicians as files 106 via programming devices 92. Files 106 may take the form of webpages 110 served to programming devices 92 by server 100. Other files, such as frequently asked questions or help files, may be created by an administrator and served by server to programming devices 92 upon request by a clinician. Such files may also take the form of webpages 110.

The distributed system allows a clinician and patient 12 to transmit and analyze programs and information from any programming device 92 capable of accessing server 100 via network 112. Allowing a clinician and patient 12 greater access to programs and information may lead to more effective and efficient therapy and use of clinician time. Patient 12 may transmit information regarding symptoms and program efficacy through a network connection in his home without having to visit a specialized clinic. Further, a clinician may be able to access patient records 98 without personal clinician/patient interaction. For example, patient 12 may experience pain in a new region of his body and indicate the location on a pain map through the user interface 72 patient programmer 26. Patient 12 may then use patient programmer 26 to transmit the information through network 112 to server 100. Database 96 stores the information as part of a record 98 for patient 12 that may be accessed by a clinician via clinician programmer 20 from a different location via network 112.

In addition to programming devices 92, computing devices 93A-N (hereinafter computing devices 93) may be used interact with server 100 according to some embodiments of the invention. Computing devices 93 may be desktop or laptop computers, workstations, personal digital assistants (PDAs), or the like. Clinicians, for example, could use a computing device 93 to access, review, and/or analyze patient records 98 at some time after the respective programming sessions for those patients. Clinicians could also use a computing device 93 to review the totality of patient records 98, seek responses to queries, study statistics 108, or view webpages 110, in order to improve their INS programming practices and techniques for future programming sessions.

Patients may be provided a level of access to server 100 via a computing device 93 for review of their patient record 98, or to view statistics 108 or webpages 110. As another example, insurers may use computing device 93 to access patient records 98 to review services provided to patients for purposes of reimbursement. Further, the information stored within database 96 and statistics 108 may be made available for analysis by academic or corporate researchers using computing devices 93. Levels of access to database 96 and files 106 via server 100 may be controlled by server 100 based on user profiles established by an administrator and stored in memory 114.

Server 100 may comprise a single computing device or processor, or a plurality of computing devices and/or processors that cooperate to provide the functionality ascribed to server 100 herein. Database 96 and files 106 may be stored within a single computing device or memory, or within a plurality of computing devices and/or memories. As shown in FIG. 5, server may include a memory 114 that stores program instructions that when executed cause server to perform the functions ascribed to server 100 herein. Memory 114 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 6:
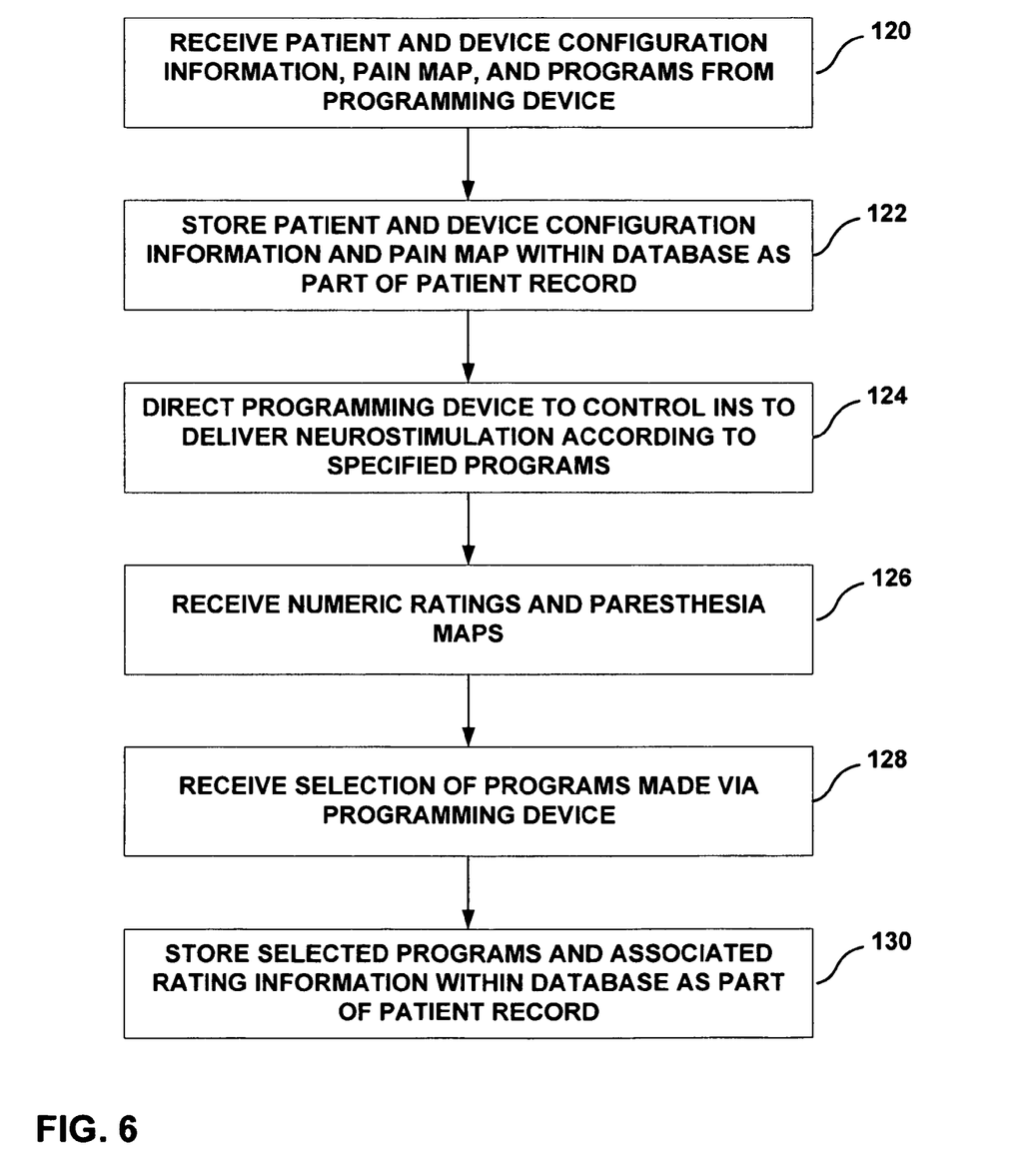
FIG. 6 is a flowchart illustrating an example method that may be employed by the server of the distributed system of FIG. 5 to interact with a programming device during a programming session.

FIG. 6 is a flowchart illustrating an example method that may be employed by server 100 interact with a clinician programmer 20, during a programming session. Server 100 receives patient information 60 and device configuration information 62 collected by a clinician via clinician programmer 20 and network 112 (120). Server 100 may also receive a pain map entered by the clinician or patient 12 using clinician programmer 20, and programs 56 specified by the clinician using programmer 20 (120). Server 100 stores patient information 60, device configuration information 62 and the pain map as part of a record 98 for patient 12 within database 96 (122).

Server 100 directs clinician programmer 20 to control INS 14 to deliver the specified programs 56 (124). In some embodiments, server 100 randomizes the order of presentation of the specified programs 56, and directs clinician programmer 20 to control INS 14 to deliver the specified programs in the randomized order. In other embodiments, server 100 generates an order of presentation that differs from the order of specification, but is non-random, that is determined according to academic and clinical research results. Server 100 receives numeric ratings and paresthesia maps entered by one or both of patient 12 and the clinician via patient programmer 20 and network 112 for each tested program (126). Server 100 may receive numeric ratings and paresthesia maps for all tested programs when testing has concluded, or for each program as the information is provided to clinician programmer 20 by a user.

In exemplary embodiments, server 100 calculates an amount of overlap for each program based on the pain map, and paresthesia map for that program. Specifically, server 100 may compare the pixel region indicated by the user on a first body template for pain to the pixel region indicated by the user on an additional body template presented during or after delivery of therapy according to a program for paresthesia provided by that program. An amount of overlap may be expressed as one or both of a percentage of the pain region covered by the paresthesia region, or a percentage of the paresthesia region not covering the pain region.

The numeric ratings, maps, and overlap amounts are rating information for the tested programs. Server 100 may provide a list of the tested programs and associated rating information to clinician programmer 20 via network 112 for presentation to the clinician. Server 100 may order the list according to the rating information, e.g., numeric ratings or amounts of overlap, and the ordering of the list may be selectably altered by the clinician. Server 100 receives indication of the programs selected by the clinician for long-term use in INS 14 (128), and stores the selected programs and the rating information associated with those programs within the record 98 for patient 12 in database 96 (130).

Figure 7:
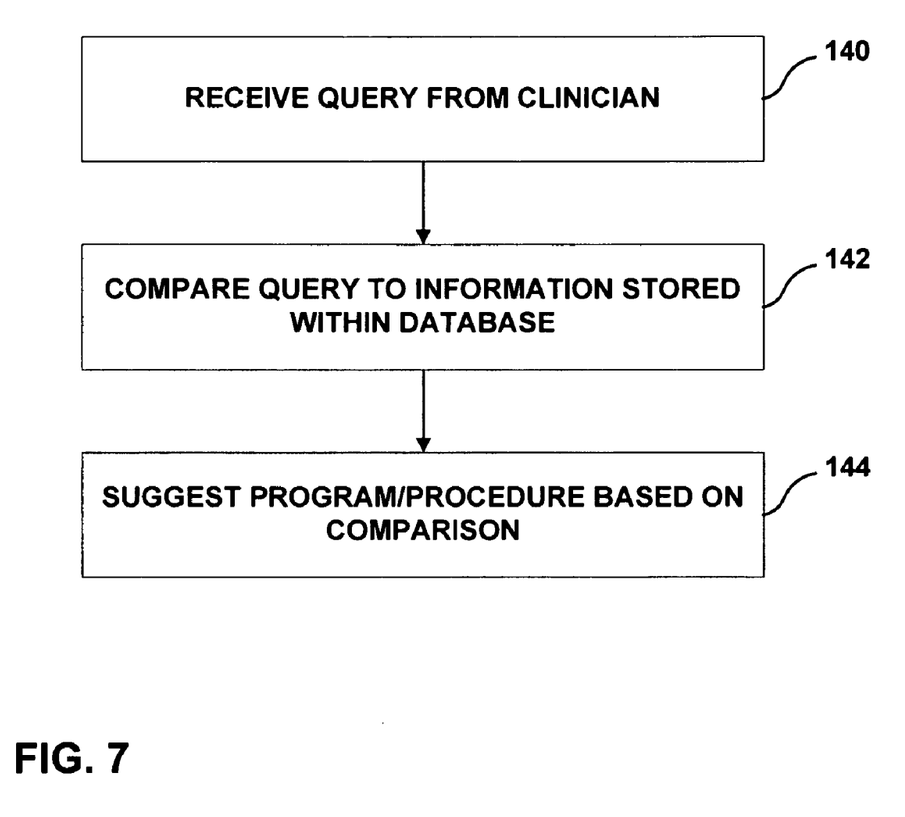
FIG. 7 is a flowchart illustrating an example method that may be employed by the server of the distributed system of FIG. 5 to respond to a query received from a clinician.

FIG. 7 is a flowchart illustrating an example method that may be employed by server 100 to respond to a query received from a clinician. In exemplary embodiments, the clinician provides the query via clinician programmer 20. In some embodiments, however, the clinician may access server 100 via network 112 using any computing device 93 in order to query server 100.

Server 100 receives a query from a clinician via a clinician programmer 20 and network 112 that includes information such as patient information 60 and device configuration information 62 (140). Server 100 compares the information of the query to information stored within database 96, and identifies one or more programs that may be effective for treatment of patient 12 and/or procedures that might be effective for identifying programs for patient 12 based on the comparison (142). Server 100 presents the identified programs and/or procedures to the clinician via clinician programmer 20 as suggestions (144). In some embodiments, server 100 may also present statistics 108 related to the suggested programs, such as percentages of a patient population that use the programs and/or consider them efficacious.

Figure 8:
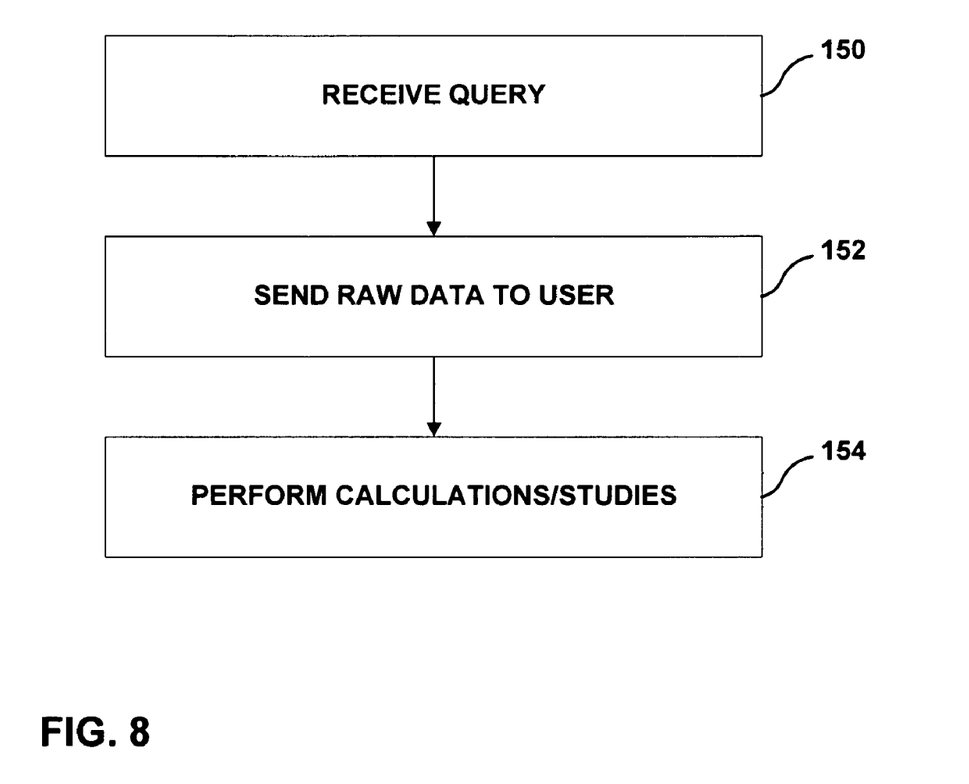
FIG. 8 is a flowchart illustrating an example method that may be employed by the server of FIG. 5 to respond to a query received from a clinician or researcher via a computing device.

FIG. 8 is a flowchart illustrating an example method that may be employed by server 100 to respond to a query received from a clinician or researcher via a computing device 93. As discussed above, clinicians and researchers may use the information stored in database 96 as a resource for investigating improvements to INS programming techniques, or neurostimulation therapy in general. Rather than performing such research using a programming device 92, researchers and clinicians may interact with server 100 to retrieve data from database 96 using a computing device 93, such as a desktop or laptop computer, that may provide more computational power for analysis of the data stored within database 96.

Server 100 receives a query for information from a user (150), and responds to the query by providing the requested information (152). Server 100 may provide raw, unanalyzed information collected during programming sessions to computing device 93, so that computing device 93 may perform an analysis (154) specified by the user, and potentially different from that which would be performed by server according to embodiments of the invention. For example, server 100 may provide raw pain and paresthesia maps within database for one or more patients, rather than rating information derived from the maps. Like server 100, computing device 93 may perform overlap calculations using the maps, but also may perform other calculations. An example of a study that could be preformed by a researcher using information stored within database 96 is a time series study, where the effect of delivery of earlier tested programs on the rating of later tested programs is studied by analysis of the paresthetia maps and numerical ratings for the various tested programs.

Figure 9:
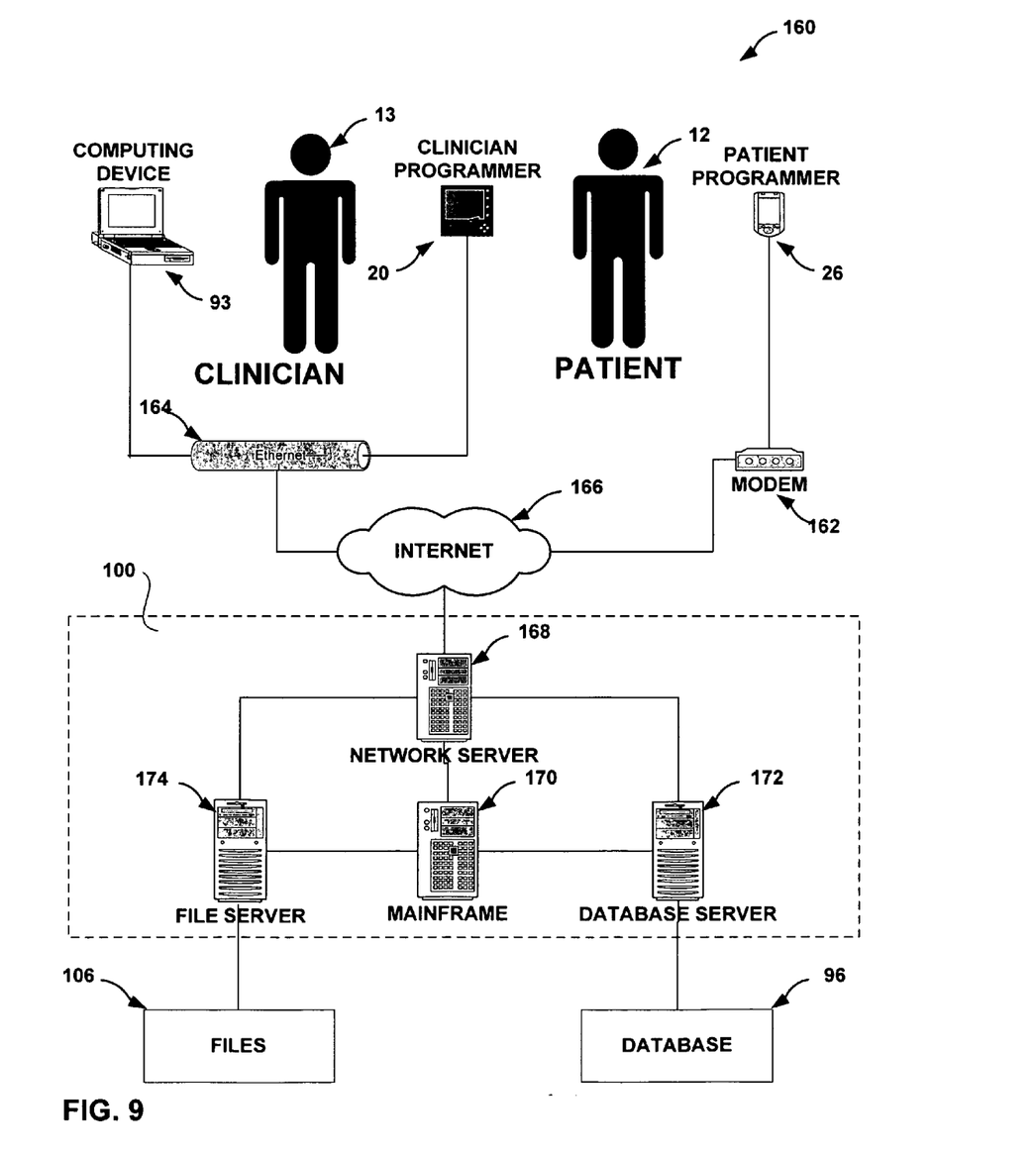
FIG. 9 is a conceptual diagram illustrating another example distributed system.

FIG. 9 is a conceptual diagram illustrating another exemplary distributed system 160. Patient 12 interacts with patient programmer 26 that communicates with network server 168 through the Internet 166 via a modem connection 162. A clinician 13 interacts with clinician programmer 20 or computing device 93 that communicates with network server 168 through the Internet 166 via an Ethernet connection 164. Network server 168 interacts with programming devices 20 and 26 and computing device 93, and also interacts with a mainframe 170, database server 172, and file server 174 to provide the functionality ascribed to server 100 above. Mainframe 170 may be a computer capable of substantial computation that analyzes information within database 96 to generate statistics 108 and other files 106. Database server 172 provides network server 168 and mainframe 170 with access to database 96, and creates and manages records within database 96. File server 174 manages files 106 and serves files to network server 168 upon request. Either or both of file server 174 and network server 168 may be web servers capable of serving web pages to client computing devices, such as programmers 20 and 26 and computing device 93.

Various embodiments of the invention have been described. These and other embodiments are within the scope of the following claims.

The invention claimed is:

1. A system comprising:
an implantable medical device configured to deliver a therapy to a patient;
a programming device that communicates with the implantable medical device; and
a server that communicates with the programming device via a network, wherein the server:
analyzes at least one of rating information for a plurality of therapy programs, each of the therapy programs defining delivery of the therapy by the implantable medical device according to the therapy program, or configuration information that indicates a configuration of the implantable medical device, wherein the configuration information comprises at least one of a device type, a number of leads, a number of electrodes, a configuration of electrodes, or positions of electrodes,
selects one of the plurality of therapy programs based on the analysis, and
indicates the selected therapy program to the programming device via the network.

2. The system of claim 1, wherein the programming device presents the selected therapy program to a user of the programming device as a suggestion.

3. The system of claim 1, wherein the programming device programs the implantable medical device to deliver the therapy according to the selected therapy program.

4. The system of claim 1, wherein the server receives at least one of the rating information or the configuration information from the programming device via the network.

5. The system of claim 4, wherein the server analyzes the at least one of the rating information or the configuration information, selects the one of the plurality of therapy programs, and indicates the selected therapy program in response to the receipt of the at least one of the rating information or the configuration information from the programming device.

6. The system of claim 1,
wherein the server receives at least one of rating information for a plurality of other patients or configuration information for a plurality of other implantable medical devices from a plurality of other programming devices via the network,
further comprising a database that stores the information received from the plurality of other programming devices, and
wherein the server analyzes at least some of the information stored in the database, and selects the therapy program based on the analysis.

7. The system of claim 6, wherein the server receives configuration information for the implantable medical device from the programming device via the network, compares the received configuration information to the configuration information stored within the database, and selects the therapy program based on the comparison.

8. The system of claim 1, wherein the rating information comprises a numerical score for at least one of the plurality of therapy programs, the numerical scores entered into the programming device or another programming device by at least one of the patient, another patient, or a clinician.

9. The system of claim 1, wherein the rating information indicates at least one of efficacy or side effects of at least one of the plurality of therapy programs.

10. The system of claim 1, wherein the server analyzes patient information in addition to the at least one of rating information for the plurality of therapy programs or configuration information that indicates a configuration of the implantable medical device, and wherein the patient information comprises at least one of symptoms, age, height, weight, or sex of the patient.

11. A method comprising
analyzing, by a server, at least one of rating information for a plurality of therapy programs, each of the therapy programs defining delivery of a therapy by an implantable medical device to the patient according to the therapy program, or configuration information that indicates a configuration of the implantable medical device, wherein the configuration information comprises at least one of a device type, a number of leads, a number of electrodes, a configuration of electrodes, or positions of electrodes;
selecting, by the server, one of the plurality of therapy programs based on the analysis; and
indicating, by the server, the selected therapy program to a programming device via a network, wherein the programming device communicates with the implantable medical device.

12. The method of claim 11, further comprising presenting, by the programming device, the selected therapy program to a user of the programming device as a suggestion.

13. The method of claim 11, further comprising programming, by the programming device, the implantable medical device to deliver the therapy according to the selected therapy program.

14. The method of claim 11, further comprising receiving at least one of the rating information or the configuration information from the programming device by the server via the network.

15. The method of claim 14, wherein analyzing the at least one of the rating information or the configuration information, selecting the one of the plurality of therapy programs, and indicating the selected program comprising analyzing, selecting and indicating by the server in response to receiving the at least one of the rating information or the configuration information from the programming device.

16. The method of claim 11, further comprising:
receiving, by the server, at least one of rating information for a plurality of other patients, patient information for a plurality of other patients, or configuration information for a plurality of other implantable medical devices from a plurality of other programming devices via the network,
storing the information received from the plurality of other programming devices within a database; and
analyzing, by the server, at least some of the information stored in the database,
wherein selecting the therapy program comprises selecting the therapy program by the server based on the analysis of at least some of the information stored in the database.

17. The method of claim 16,
further comprising receiving at least one of patient information for the patient or the configuration information for the implantable medical device by the server from the programming device via the network,
wherein analyzing the at least one of the patient information or the configuration information comprises comparing the received at least one of patient information and configuration information to at least one of the patient information and configuration information stored within the database, and
wherein selecting the therapy program comprises selecting the therapy program by the server based on the comparison.

18. The method of claim 11, wherein the rating information comprises a numerical score for each of the programs, the numerical scores entered into the programming device or another programming device by at least one of the patient, another patient, or a clinician.

19. The method of claim 11, wherein the rating information indicates at least one of efficacy or side effects of each of the programs.

20. The method of claim 11, wherein analyzing, by the server, at least one of rating information for the plurality of therapy programs, each of the programs defining delivery of the therapy by the implantable medical device to the patient according to the program, or configuration information that indicates the configuration of the implantable medical device further comprises analyzing, by the server, patient information, and wherein the patient information comprises at least one of symptoms, age, height, weight, or sex of the patient.

21. A system comprising:
means for delivering a therapy to a patient;
means for programming the implantable medical device;
means for communicating with the means for programming via a network, wherein the means for communicating comprises:
means for analyzing at least one of rating information for a plurality of therapy programs, each of the programs defining delivery of the therapy according to the program by the means for delivering or configuration information that indicates a configuration of the means for delivering, wherein the configuration information comprises at least one of a device type, a number of leads a number of electrodes a configuration of electrodes or positions of electrodes,
means for selecting one of the plurality of therapy programs based on the analysis, and
means for indicating the selected program to the means for programming via the network.

* * * * *